(12) United States Patent
Rhodes et al.

(10) Patent No.: US 9,027,384 B2
(45) Date of Patent: May 12, 2015

(54) GAS CHROMATOGRAPH PROVIDING SEMI-AUTOMATIC IDENTIFICATION OF CONNECTED SAMPLE FLOW COMPONENTS, AND METHOD OF OPERATING SAME

(75) Inventors: Robert P. Rhodes, Lincoln University, PA (US); William H. Wilson, Newark, DE (US)

(73) Assignee: Agilent Technologies, Inc., Santa Clara, CA (US)

( * ) Notice: Subject to any disclaimer, the term of this patent is extended or adjusted under 35 U.S.C. 154(b) by 861 days.

(21) Appl. No.: 13/193,436

(22) Filed: Jul. 28, 2011

(65) Prior Publication Data
US 2013/0025347 A1     Jan. 31, 2013

(51) Int. Cl.
*G01N 30/88*     (2006.01)

(52) U.S. Cl.
CPC ..................... *G01N 30/88* (2013.01)

(58) Field of Classification Search
CPC .................................................. G01N 30/88
USPC ............................................. 73/23.35, 23.39
See application file for complete search history.

(56) References Cited

U.S. PATENT DOCUMENTS 7,178,416 B2 *    2/2007    Whelan et al. ............. 73/864.91

OTHER PUBLICATIONS

"Using ChemStation Plus and Agilent Column ID Tags for Easier Handling and Compliance in Regulated Laboratories", Agilent Technologies, Inc., www.agilent.com/chem/nds, Oct. 1, 2002, 4 pp.
Acquity UPLC HSS Columns—Care and Use Manual, Waters Corporation, www.waters.com, May 2009, 9 pp.

* cited by examiner

*Primary Examiner* — Daniel S Larkin

(57) ABSTRACT

A method for semi-automatically generating configuration information for a gas chromatograph uses an identification device reader of the gas chromatograph to 1) determine a presence and location of sample flow component identification devices in or on identification device holders that hold the sample flow component identification devices; 2) read information from sample flow component identification devices held in the identification device holders; and 3) output configuration information for the gas chromatograph. The configuration information is based on the presence and location of particular sample flow component identification devices in or on particular identification device holders, and on associations of particular identification device holders with particular sample flow component connections to the gas chromatograph. The configuration information indicates if and how sample flow components are connected to the gas chromatograph.

24 Claims, 12 Drawing Sheets

GAS CHROMATOGRAPH PROVIDING SEMI-AUTOMATIC IDENTIFICATION OF CONNECTED SAMPLE FLOW COMPONENTS, AND METHOD OF OPERATING SAME

BACKGROUND

Gas chromatograph (GC) columns are usually identified by a metal tag fastened to the column basket or holder. These tags list the column part number, serial number, size and information about the phase, type and thickness. For standard GC columns, these tags are in the oven with the column and so are not readable unless the column oven door is opened. For a new type of column, a Low Thermal Mass or LTM column, the tag is fastened to a cover around the column, but this may be hidden by a protective cover during use, While the tags attached to columns may contain all of the information needed to operate the columns in the instruments in which they are installed, the information on the tags must be manually entered into the GC or an interfaced computer in order to make use of the information.

BRIEF DESCRIPTION OF THE DRAWINGS

Illustrative embodiments of the invention are illustrated in the drawings, in which.

DETAILED DESCRIPTION

The following description describes certain improvements to a gas chromatograph. Some of the improvements pertain to the semi-automatic identification of "sample flow components" connected to a gas chromatograph, and in some cases, to the semi-automatic identification of sample flow components connected to "sample flow ports" of a gas chromatograph.

Figure 1:
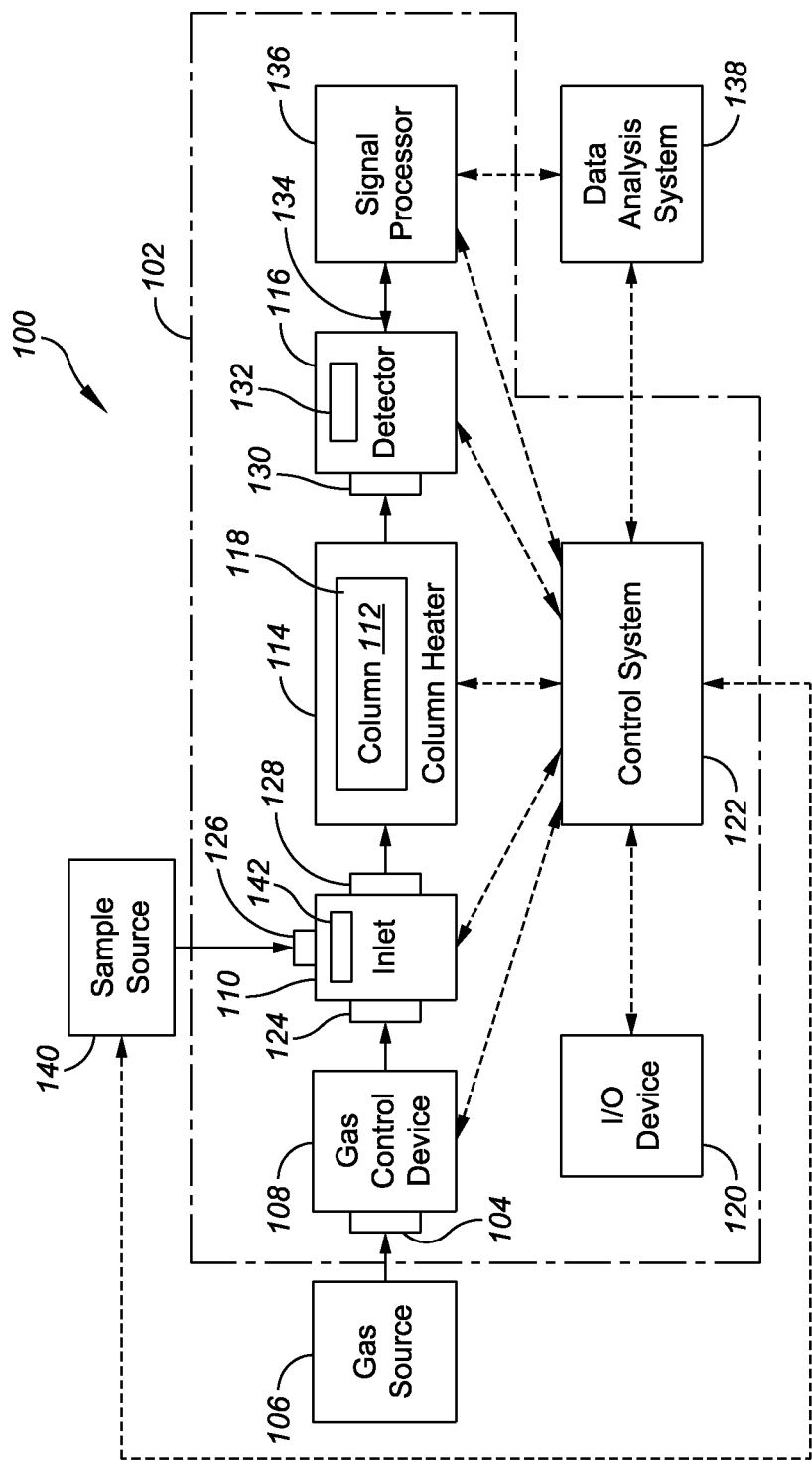
FIG. 1 provides an example of a block diagram of a GC system.

So that the reader may better understand the disclosed improvements to a gas chromatograph, this description begins with a discussion of gas chromatographs in general, and provides examples of some of the typical components found in a gas chromatograph. A block diagram of a gas chromatographic system 100 (including a gas chromatograph 102) is shown in FIG. 1. Solid lines with arrows (in FIG. 1) represent fluid flow, whereas dotted lines with arrows represent electrical data flow. The blocks within the dashed/dotted boundary represent the typical minimum set of components needed to define the gas chromatograph portion 102 of a gas chromatographic system 100. It is noted, however, that a GC manufacturer or distributor may in some cases make or sell a unit that does not have all of the components shown in FIG. 1, with the expectation that a purchaser or user may 1) not need all of the components, or 2) separately purchase or provide some of the components. For purposes of this description, units that include all of the GC components but for those which a purchaser or user might self-install or find optional are also referred to as GCs.

A gas chromatograph (GC) 102 is a device that separates and detects components in a mixture. A typical GC 102 includes:

1) A pressurized gas input 104, connectable to a source of pressurized gas 106 (typically external to the GC 102) that is used as a carrier gas.
2) A device 108 to control the flow of the carrier gas in the GC 102.
3) An net 110 having a means to introduce a sample into the carrier gas,
4) A column 112 through which the carrier gas and sample flow.
5) A device 114 to control the temperature of the column 112.
6) A detector 116 at the gas exit end 118 of the column 112, which detector 116 responds to sample components differently than carrier gas.
7) An input/output device 120 via which control set points can be input and GC parameter values can be monitored.
8) A control system 122 for controlling the various devices that constitute the GC 102.

Each of the above GC components is described below in more detail.

In many cases, the pressurized gas input 104 is simply a connector or fitting to which the source of pressurized gas 106 is connected. By way of example, the source of pressurized gas 106 can be a pressurized cylinder of a suitable gas or a gas generator. A gas generator might take the form of an aft compressor with a separation device that separates nitrogen from other air components, thus providing a source of nitrogen. A gas generator could also take the form of a hydrogen generator and separator, wherein the hydrogen generator uses electrolysis to convert water to hydrogen and oxygen, and wherein the separator separates the hydrogen from the oxygen. The gas generator could also take other forms, and for a limited set of columns, the gas generator could be a simple air compressor.

The pressure of the pressurized gas (the carrier gas) may in some cases be regulated, or at least partially regulated, by a pressure regulator provided on the source of the pressurized gas. However, a GC 102 will typically include a device 108 (e.g., a pressure regulator or one or more valves) to control the pressure or flow of carrier gas in the GC 102. In cases where a mechanism for controlling the pressure or flow of the gas is provided at the source of pressurized gas, the GC's device 108 may provide secondary control of the pressure or flow of the gas. Control can be purely mechanical, or it can take other forms. For example, the GC's control device 108 can be an electro-mechanical system with sensors and feedback control. Today's GCs typically include the latter type of system, with control involving a digital control system 122 using some kind of processing device to control a valve or valves based on the signal(s) received from the sensor(s).

The type of sample introduction system or "inlet" 110 employed by a GC 102 depends on the characteristics of the sample to be introduced. A gas sample can be introduced by filling a volume with the sample (at a known temperature and pressure) and then directing the carrier gas through this volume on its way to the column 112. A rotary gas sampling valve is the usual approach. An alternative approach for gas samples is to use a gas tight syringe as the fill volume, and to inject the sample into the carrier gas by introducing the syringe needle into the flow (or stream) of carrier gas through a suitable pressure locking device (a rubber septum being the common example). The plunger of the syringe is then depressed to inject the sample into the carrier gas stream. Liquid samples are usually introduced using a syringe, again with the needle entering the carrier gas stream without allowing significant leakage between the carrier gas stream and the atmosphere. The usual means for preventing leakage is a rubber septum. The liquid sample is then vaporized by heating it. This can be done in the column itself by heating the column, or can be done in a separate area before the column 112, which separate area is heated independently of the column 112.

For purposes of this description, an "inlet" 110 is defined to include one or more components (i.e., inlet components) which singularly or in combination define: a carrier gas input port 124, a sample flow injection port 126, a column connection port 128 (i.e., a column head connection port) through which the carrier gas and injected sample flow, and any additional port(s) 142 for receiving replaceable inlet components (e.g., inlet liners).

The column 112 is the device where sample separation occurs. The column 112 contains material that is not vaporized and that interacts with different sample components differently. A typical column 112 is a capillary tube with a coating of a suitable polymer film on its walls. Columns can also contain particles that may interact with the sample—either directly, or because of a coating on the particles. The material that interacts with the sample components is known as the stationary phase. In any case, as the sample components flow through the column 112, some of the sample components interact more strongly with the stationary phase than others and are retained for longer times. Ultimately, the sample components are carried by the carrier gas to the gas exit end 118 (detector end) of the column 112, where they exit the column 112 at different times depending on the differences in their interactions with the stationary phase.

The sample component interactions with the column stationary phase can usually be adjusted by controlling the temperature of the column 112. This typically takes the form of a column temperature control or heating device 114 (e.g., a column heater). In many mixtures, some sample components interact very little with the column 112 at a given temperature, while other sample components would be retained indefinitely at that same temperature. For this reason, a GC 102 typically has a device 114 for controlling the temperature of the column, which device 114 allows the column temperature to be changed in a controlled (and repeatable) way while the sample components are migrating through the column 112. Given the nature of the interactions, this almost always involves increasing the temperature of the column 112 during sample elution. When the last sample component has eluted from the column 112, the temperature must be returned to the starting temperature before the next sample can be introduced. For some samples, the desired starting temperature of the column 112 may be below room temperature; for some it may be at or near room temperature; and for others, it may be higher than room temperature.

GC detectors 116 typically provide a change in an electrical signal when some or all sample components elute from the column 112. Some detectors use physical properties of the molecules to distinguish them. The usual example of this is a thermal conductivity detector. This form of detector monitors the thermal conductivity of the gas going through it. If the thermal conductivity of a sample component differs from that of the carrier gas, a signal is generated. Other detectors rely on some sort of chemical reaction to generate a new species that provides an electrical signal. Many detectors rely on some kind of ionization process, with the carrier gas not being ionized, and sample molecules being ionized with some efficiency. The ionization is measured as an electrical signal—usually by simply collecting the ions and monitoring the ion current. There are also detectors that cause certain sample molecules to convert to an excited form that emits a photon. The photons are then detected using an appropriate device, such as a photomultiplier tube in which they are converted to an electrical signal. Detectors usually involve additional gases—either as reactants or simply as sweep flows. Control of these gases can be critical and is typically accomplished by some form of electromechanical system. Specific examples of detectors include, but are not limited to, flame ionization detectors, nitrogen/phosphorous detectors, flame photometric detectors, and mass spectrometers. Replaceable components of these detectors can include, for example, detector jets, detector beads and detector filters.

For purposes of this description, a "detector" 116 is defined to include one or more components (i.e., detector components) which singularly or in combination define: a column connection port 130 (i.e., a port for receiving the gas exit end 118 of a column 112) through which the carrier gas and injected sample flow, any additional port(s) 132 for receiving replaceable detector components (e.g., detector jets, detector beads or detector filters), and a signal output 134 that provides one or more signals representing detection of one or more sample components.

Also for purposes of this description, the concept of a "sample flow port" is introduced. Sample flow ports may take various forms, and include those ports through which a sample or sample component can flow—either alone, or in combination with a carrier gas. Sample flow ports therefore include, for example, ports such as: a sample flow injection port on an inlet, a column connection port on an inlet, a column connection port on a detector, and in some cases, a port for receiving a replaceable inlet or detector component.

Another concept introduced in this description is that of a "sample flow component". A sample flow component is any component through which a sample or sample component can flow—either alone, or in combination with a carrier gas. Sample flow components therefore include, for example, components such as: a sample injection syringe, an inlet, certain inlet components, an inlet liner, a pre-column, a column, a detector, certain detector components, a detector filter, and any connectors or fittings for coupling these components to (or otherwise installing them in) a GC. A sample flow component may also take the form of a combined inlet, detector and column assembly.

The input/output device 120 (or devices) can include analog switches and indicators, but more commonly includes a keyboard and display of some form. Alternatively, control set points can be input, and system parameter values can be monitored, using an external computer and appropriate software. The external computer and software can then be used to control and monitor from one to several GCs. The same external computer may be used to perform some or all of the data analysis for the one or more GCs.

The control system 122 usually includes a signal processor 136 of some sort that can calculate how to change parameters (or control elements) of the GC 102 based on current values and desired values of the parameters being controlled. The control system 122 may comprise one or many signal processors, which may take the form of conventional microprocessors, external computers, field programmable gate arrays, digital signal processors, or any other suitable device or combination of devices. Analog control devices can also be used for control of some or all of a GC's components. The control system 122 will also typically provide a storage device (or storage devices) to store control set points.

A gas chromatographic system 100 adds to a GC 102 a means to evaluate the electrical signals generated by the detector and relate them to the amounts and identities of the sample components. This usually involves a computer and software. Depending on how the detector signal is output (digital or analog), it may also include an analog to digital converter or other signal processor. The computer plus software is usually referred to as a "chromatographic data analysis system" 138. The chromatographic data analysis system 138 is often separate from the GC 102, and in some cases may be communicatively coupled with the GC 102 over a local area network, a wide area network, the Internet, or some other communication means (including, for example, a point-to-point or shared bus serial connection). The chromatographic data analysis system 138 can also be provisioned as part of the GC 102, and with or without a normal computer keyboard and display.

A gas chromatographic system 100 may also add a means to store samples and automatically introduce them to the GC 102. This is generalized as the "sample source" 140 in FIG. 1. In some cases, the sample source may include or operate the afore-mentioned rotary valve or syringe.

FIG. 1 illustrates a fairly simple GC 102 in that only one inlet 110, column 112, detector 116 and column heating device 114 is shown. However, many GCs have two inlets and/or two detectors, and in fact, a GC with any number of inlets and any number of detectors is possible. A GC is also typically capable of processing samples through more than one column, in addition to processing samples through components such as inlet liners and pre-columns.

When a GC is capable of receiving more than one column, the columns are typically connectable to the GC in different ways. For example, columns may be connected together in series between a particular inlet and detector, or connected so that a sample partially separates in one column, with some peaks being sent to another column for further separation. Columns may also be connected in other ways, and in different column combinations, between various pairings of a GC's inlet(s) and detector(s). In some cases, a GC's columns can be connected to the GC to define a plurality of (i.e., two or more) sample flow paths.

Because GCs may process samples through more than one column or sample flow path, GCs sometimes employ more than one column heating device, thereby enabling different columns and pre-columns to be heated to different temperatures.

From the above description of GC systems, it should be clear that GC systems, including configurations of the GC itself, can get quite complicated.

Figure 2:
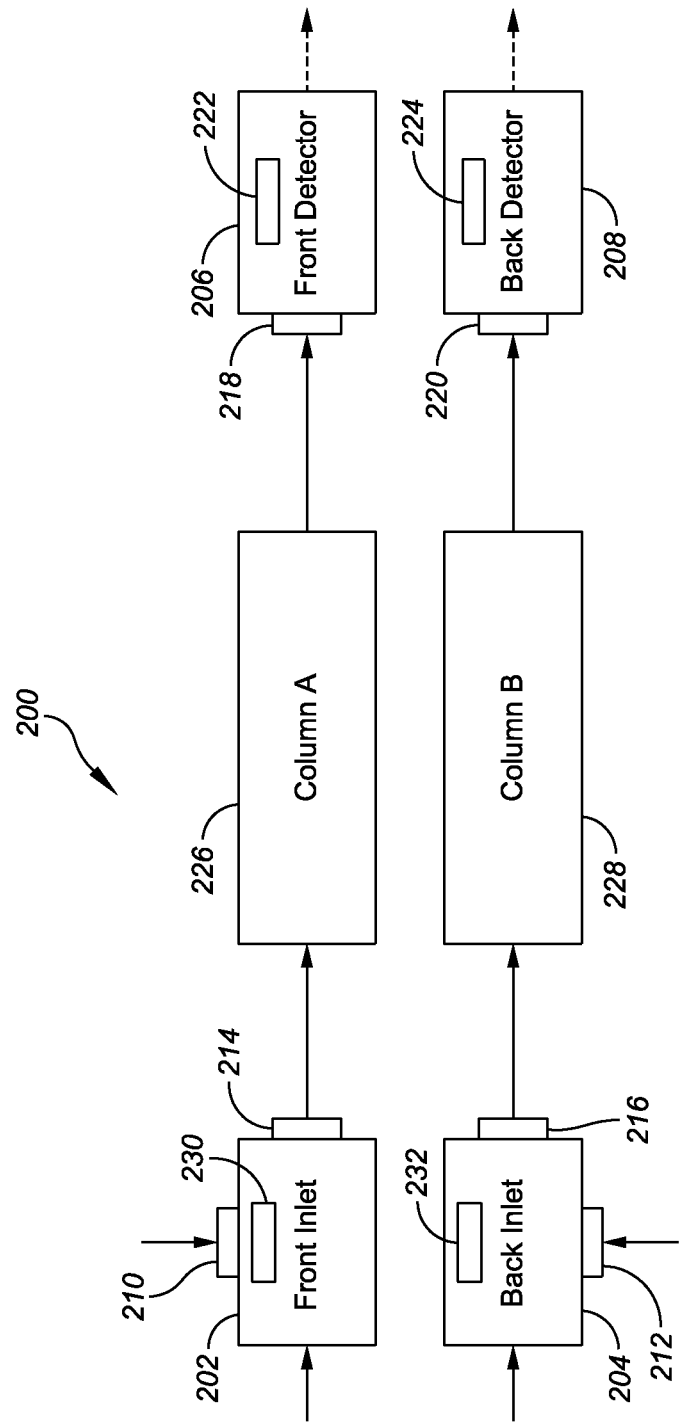
FIG. 2 illustrates components of a relatively simple GC having two inlets and two detectors, and provides a first example of how sample flow components can be connected to the inlets and detectors.
Figure 3:
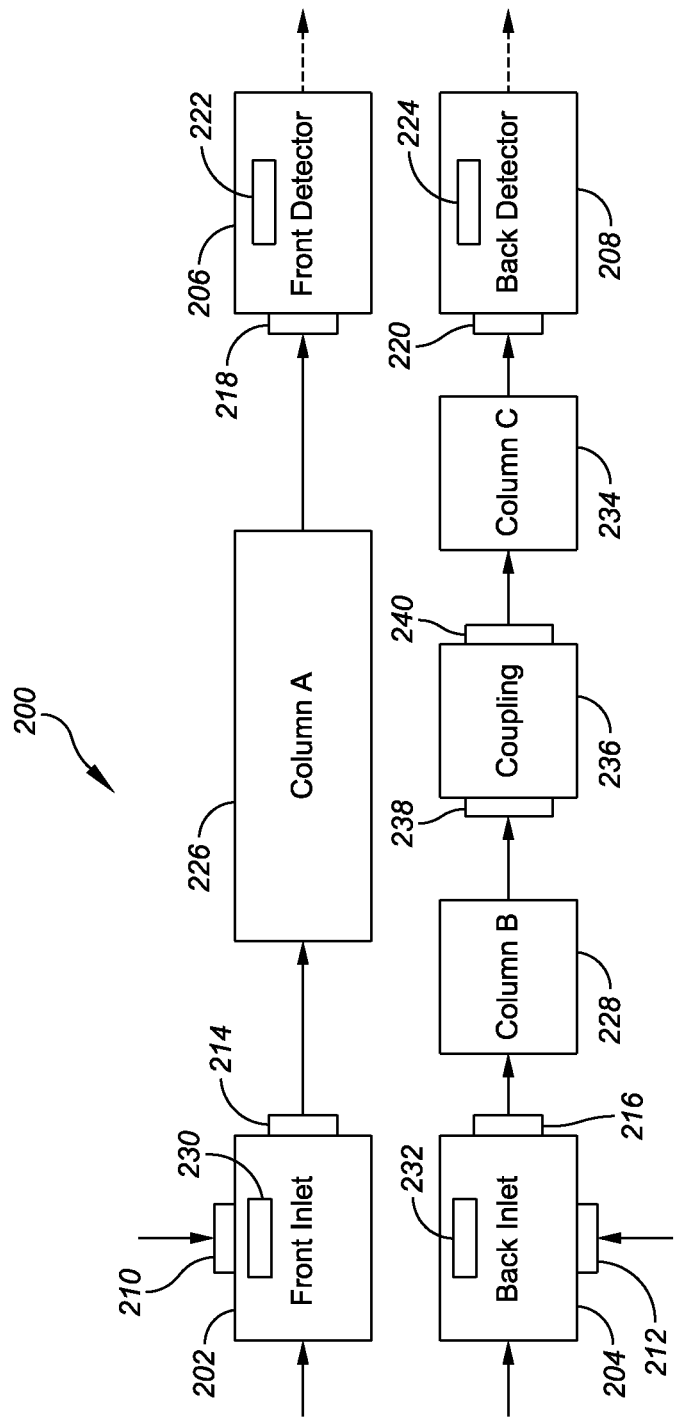
FIG. 3 provides a second example of how sample flow components can be connected to the inlets and detectors shown in PG. 2.
Figure 4:
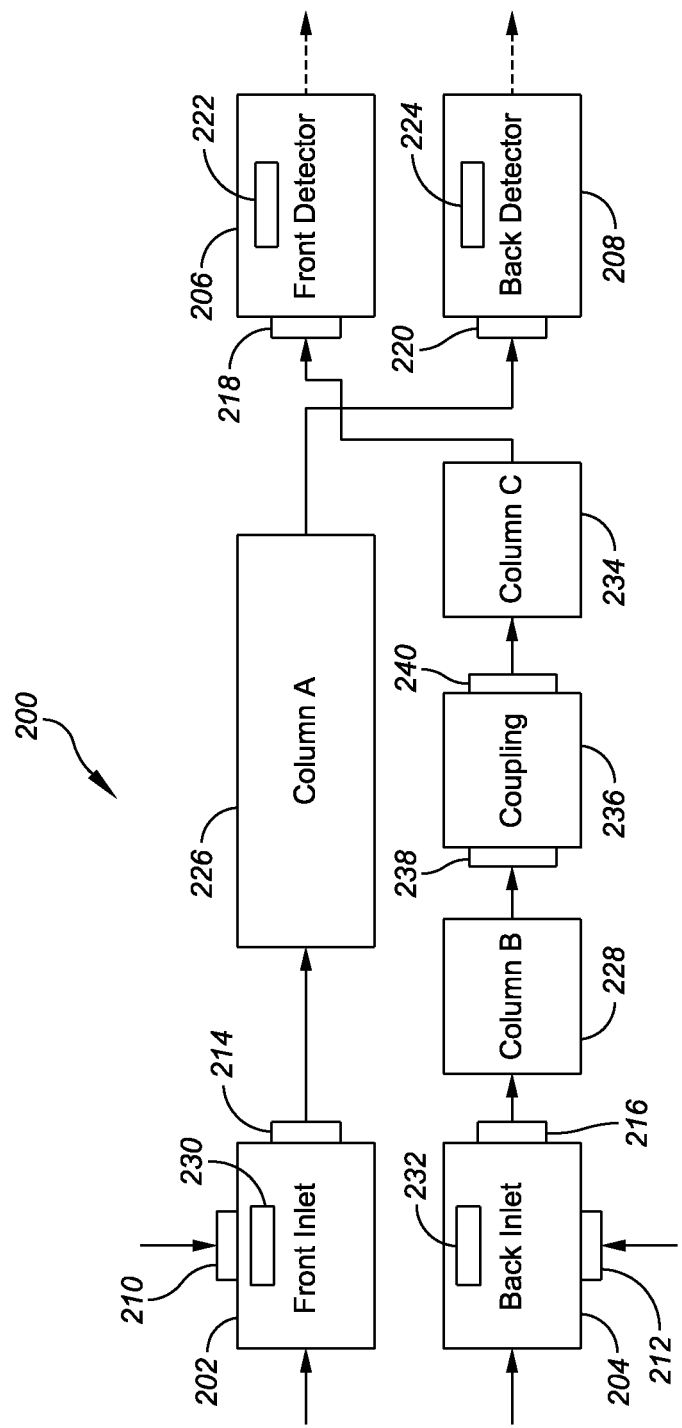
FIG. 4 provides a third example of how sample flow components can be connected to the inlets and detectors shown in FIG. 2.
Figure 5:
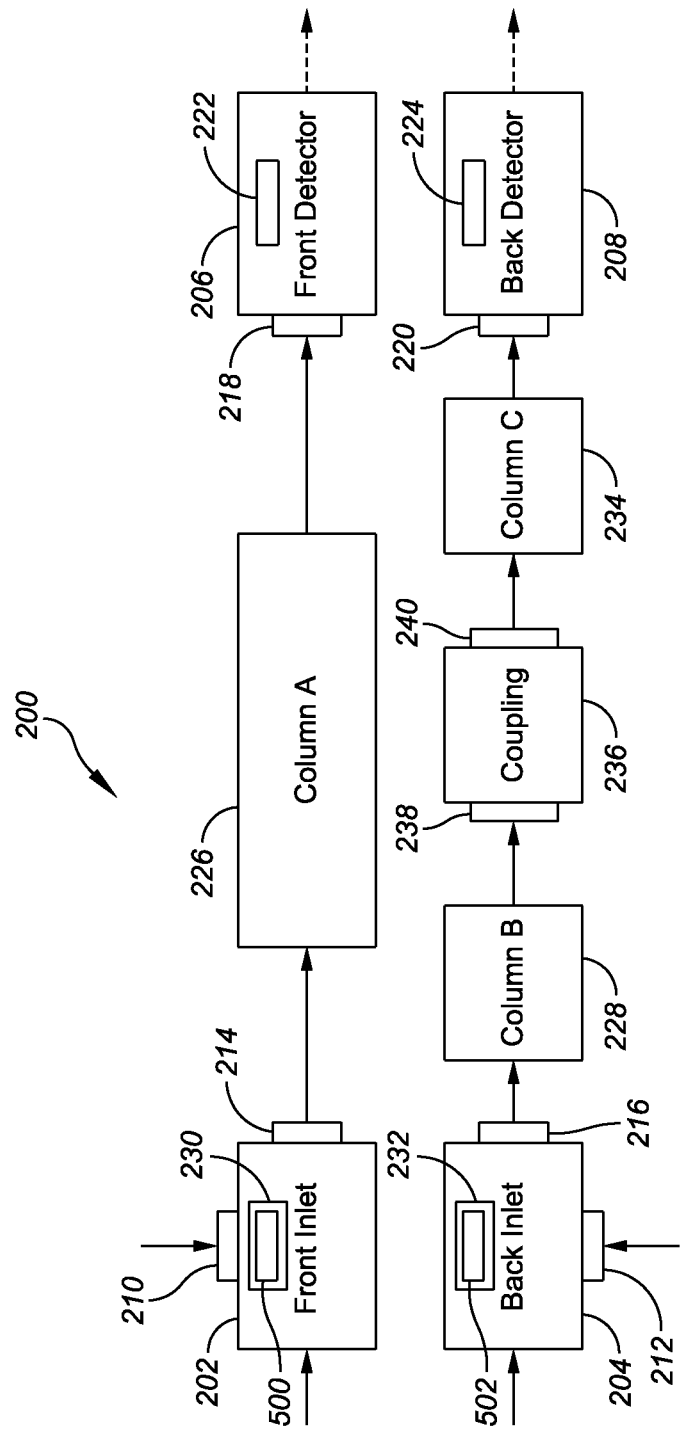
FIG. 5 provides a fourth example of how sample flow components can be connected to the inlets and detectors shown in FIG. 2.

To properly control the carrier gas flow through a GC's columns, information is needed on "what" columns are connected to the GC (e.g., column presence information), and "how" the columns are connected (e.g., column location information). Consider a GC having two inlets and two detectors. The inlets 202, 204 and detectors 206, 208 of such a GC 200, as well as the sample flow ports 210, 212, 214, 216, 218, 220, 222, 224, 230, 232 of the inlets 202, 204 and detectors 206, 208, are shown in FIG. 2. As shown in FIG. 2, a Column A 226 can be connected between the Front Inlet 202 and the Front Detector 206, and a Column B 228 can be connected between the Back Inlet 204 and the Back Detector 208. Or, as shown in FIG. 3, a Column A 226 can be connected between the Front Inlet 202 and the Front Detector 206; a Column B 228 can be connected to the Back Inlet 204; and a Column C 234 can be connected between the Column B 228 and the Back Detector 208. Or, as shown in FIG. 4, the Column A 226 can be connected between the Front Inlet 202 and the Back Detector 208; the Column B 228 can be connected to the Back Inlet 204; and the Column C 234 can be connected between the Column B 228 and the Front Detector 206. Or, as shown in FIG. 5, an Inlet Liner A 500 can be installed in a sample flow port 230 of the Front Inlet 202; the Column A 226 can be connected between the Front Inlet 202 and the Front Detector 206; an Inlet Liner B 502 can be installed in a sample flow port 232 of the Back Inlet 204; the Column B 228 can be connected to the Back Inlet 204; and the Column C 234 can be connected between the Column B 228 and the Back Detector 208. Typically, two columns (e.g., Columns B & C 228, 234) will be joined by a coupling 236 or other sample flow component having first and second sample flow ports 238, 240 (and possibly other sample flow ports—e.g., to introduce additional gas flows).

The sample flow components shown in FIGS. 2-5 can also be connected in other ways, and may be connected in combinations with more, fewer or different types of sample flow components. For example, there are hundreds of types of columns that can be connected in the above configurations. Information about the specific types of columns being connected to a GC needs to be known. This information includes, for example, the dimensions of the columns and the types of stationary phases used in the columns. To further complicate matters, there are column parameters that a user can change. For example, a user may periodically change the length of a column by cutting off a few centimeters to few meters. In order to obtain useful data from a gas chromatograph experiment, this change in a column's length needs to be documented and input to the GC.

Today, when a column is installed in a GC, the user must manually configure the GC by inputting into the GC (or a connected computer) information about the column and the way it is connected. Typically, this information is input via buttons, knobs or other input devices on the front panel of the GC (or via a keyboard attached to the GC). This manual entry of column connection information is error prone. In some cases, a user may forget to input new connection information when a column or its connections to the GC are changed.

Other devices that a user may change without notice, and that will seriously impact his or her results, include the sample injection syringe (typically operated by an automated system) and the liner in the inlet. If the GC system has been told the wrong syringe volume, it will inject the wrong volume of sample. If the GC system has been told the wrong inlet liner, or if the wrong inlet liner has been installed, a sample may not be properly vaporized, or non-volatile components that tend to damage a column may not be trapped. Detector types and details also need to be known. In some cases, a detector may be more permanently affixed within a GC system, and its details may be known to the GC system in the absence of configuring the GC system. However, in other cases, a detector may need to be added to the GC system, and details of the detector will need to be provided to the GC system as part of the GC configuration process.

Figure 6:
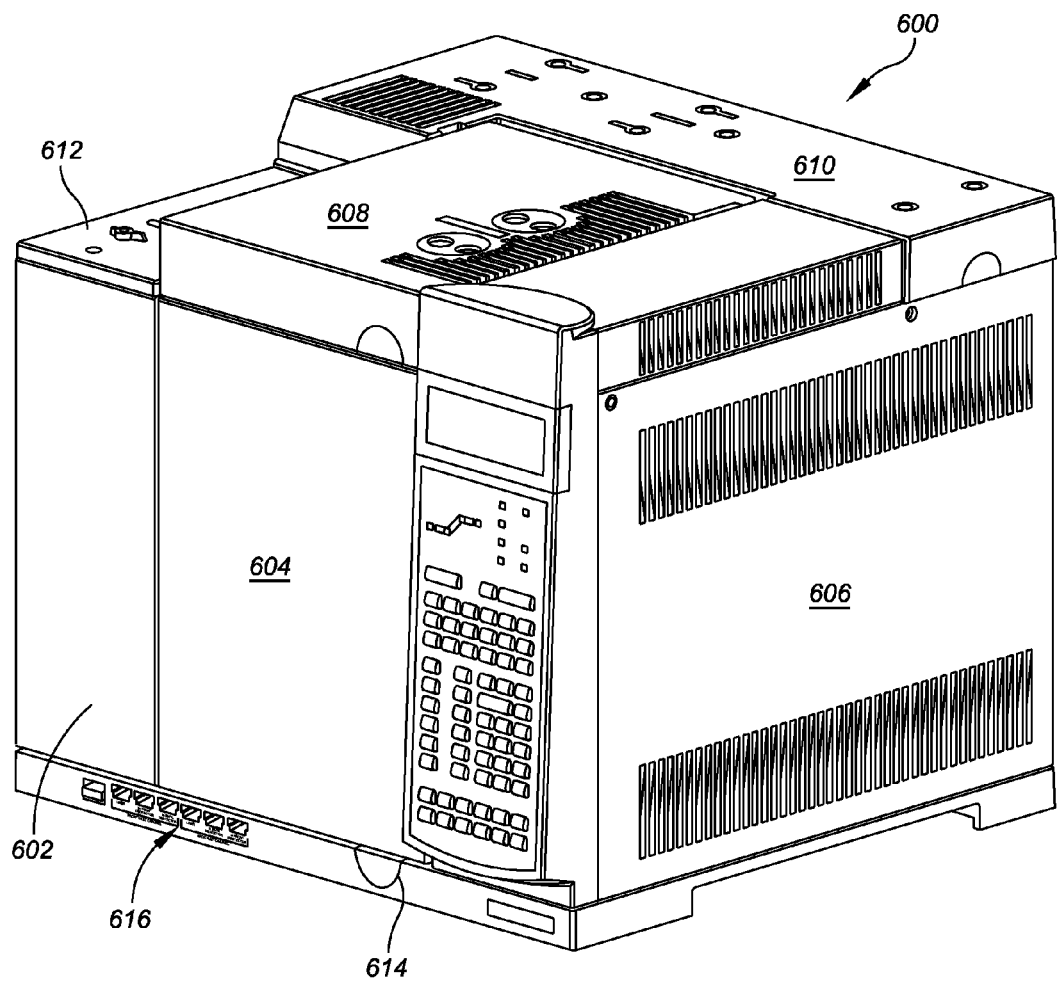
FIG. 6 illustrates an example of a GC having features for at least partially automating the identification of columns and their connections.

Given the above context, FIG. 6 illustrates a GC 600 having features for at least partially automating the identification of columns and their connections.

Figure 7:
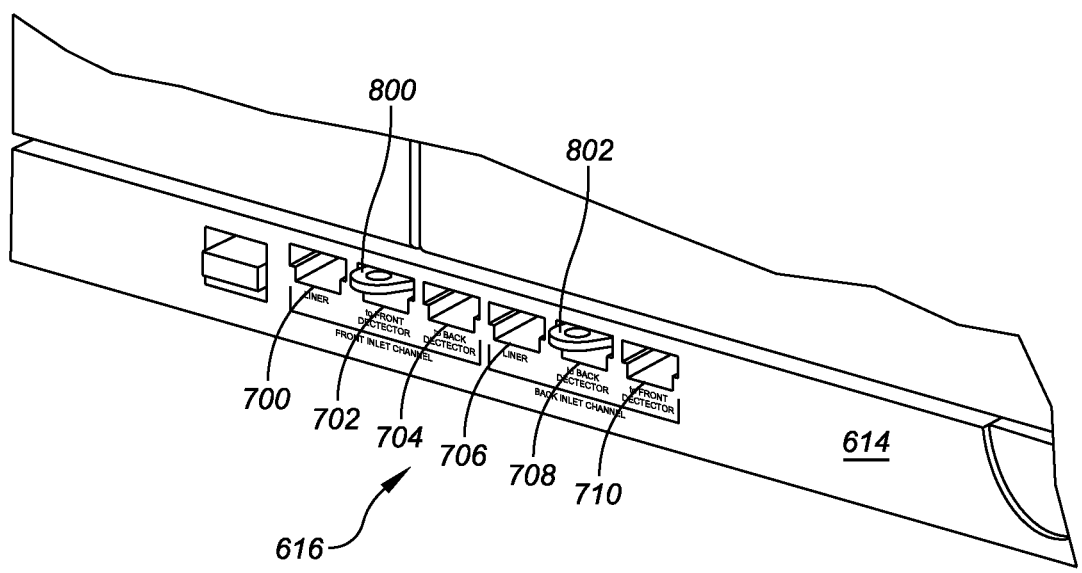
FIG. 7 provides a close-up perspective view of the bays shown in FIG. 6, and illustrates a number of fobs held in particular ones of the bays.

FIG. 6 provides a perspective view of a GC 600 having a housing 602 to which the sample flow components illustrated in FIG, 2 are mounted. The housing 602 includes a plurality of body panels 604, 606, 608, 610, 612 and 614 mounted to an internal frame (not visible). The body panels 604, 606, 608, 610, 612, 614 conceal the sample flow components from view in FIG. 6. Defined within the front panel 614 of the GC 600 is a plurality of slots 616 that provide access to a plurality of bays. Each of the bays is configured to hold a fob associated with a sample flow component connected to the GC 600. FIG. 7 provides a close-up perspective view of the slots 616 and bays 700, 702, 704, 706, 708, 710, and illustrates a number of fobs 800, 802 held in particular ones 702, 708 of the bays 700, 702, 704, 706, 708, 710.

Figure 8:
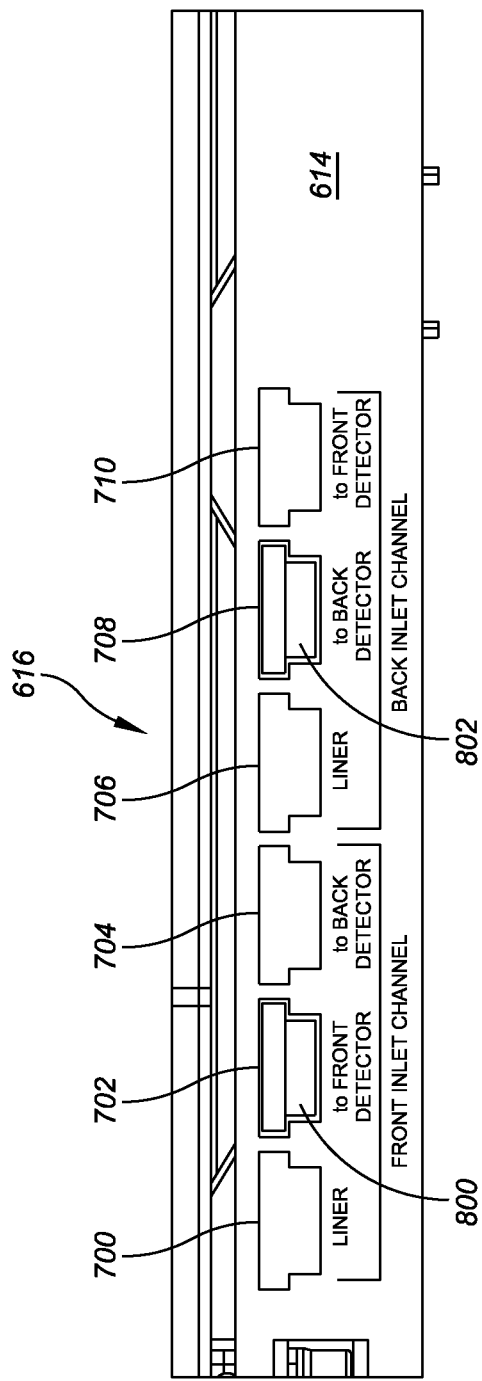
FIG. 8 illustrates a close-up elevation of the bays shown in FIG. 6, and illustrates a number of fobs held in particular ones of the bays.

A close-up elevation of the slots 616 and bays 700, 702, 704, 706, 708, 710 is shown in FIG. 8. FIG. 8 also illustrates various textual descriptions associated with the bays 700, 702, 704, 706, 708, 710. A first group of bays 700, 702, 704 is identified as being associated with sample flow components that are connected to a FRONT INLET CHANNEL of the GC 600, and a second group of bays 706, 708, 710 is identified as being associated with sample flow components that are connected to a BACK INLET CHANNEL of the GC 600. Referring to the sample flow components shown in FIG. 2, the FRONT INLET CHANNEL includes the Front Inlet 202 and the Front Detector 206, whereas the BACK INLET CHANNEL includes the Back Inlet 204 and the Back Detector 208. Included within the bays 700, 702, 704, 706, 708, 710 for each channel of the GC 600 are bays 700, 706 corresponding to installations of inlet liners (LINER) in the inlets 202, 204 of the channels, as well as bays 702, 704, 708, 710 corresponding to connections of columns between respective ones of the inlets 202, 204 and detectors 206, 208 (Le., a bay 702 for installation of a column between the FRONT INLET and FRONT DETECTOR of the GC 600; a bay 704 for connection of a column between the FRONT INLET and BACK DETECTOR of the GC 600; a bay 708 for connection of a column between the BACK INLET and BACK DETECTOR of the GC 600; and a bay 710 for connection of a column between the BACK INLET and FRONT DETECTOR of the GC 600).

When fobs associated with particular sample flow components are placed in particular ones of the bays 700, 702, 704, 706, 708, 710, the GC 600 1) determines the presence and location of the fobs in the bays, 2) reads information from the fobs, including information that identifies the sample flow components with which the fobs are associated, and 3) generates configuration information for the GC 600. The configuration information is based on the presence and location of particular fobs in particular ones of the bays, and on the associations of A) particular bays with B) particular connections of sample flow components to the GC 600 or its sample flow ports.

The particular arrangement of fobs 800, 802 shown in FIG. 8 indicates that a first column 226 connects the front inlet 202 of the GC 600 to the front detector 206 of the GC 600; and that a Column B 228 connects the back inlet 204 of the GC 600 to the back detector 208 of the GC 600 (see also, FIG. 2). By inserting fobs in different ones or groups of the bays 700, 702, 704, 706, 708, 710, different configurations of the GC 600 can be specified.

The bays 700, 702, 704, 706, 708, 710 shown in FIGS. 7 & 8 are one example of what is more generally referred to herein as a plurality of "identification device holders". In some non-limiting examples, said plurality is from 2 to 12, or 2 to 10, or 2 to 8, or 2 to 6, or 2 to 4. In some cases, identification device holders may take other forms. These forms include, for example, shelves, pockets, sockets, mechanical or electrical connectors, and magnetic holders.

Figure 9:
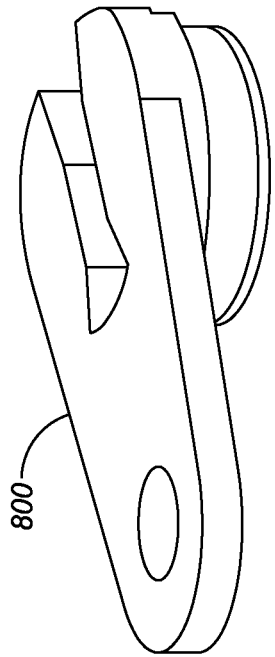
FIG. 9 illustrates an example of one of the fobs shown in FIG. 8.

The fobs 800, 802 shown in FIGS. 7 & 8 are one example of what is more generally referred to herein as a plurality of "sample flow component identification devices". The sample flow component identification devices may take various physical forms, including forms such as fobs, cards, tags, chips or keys. FIG. 9 illustrates an example of one particular fob 800.

Figure 10:
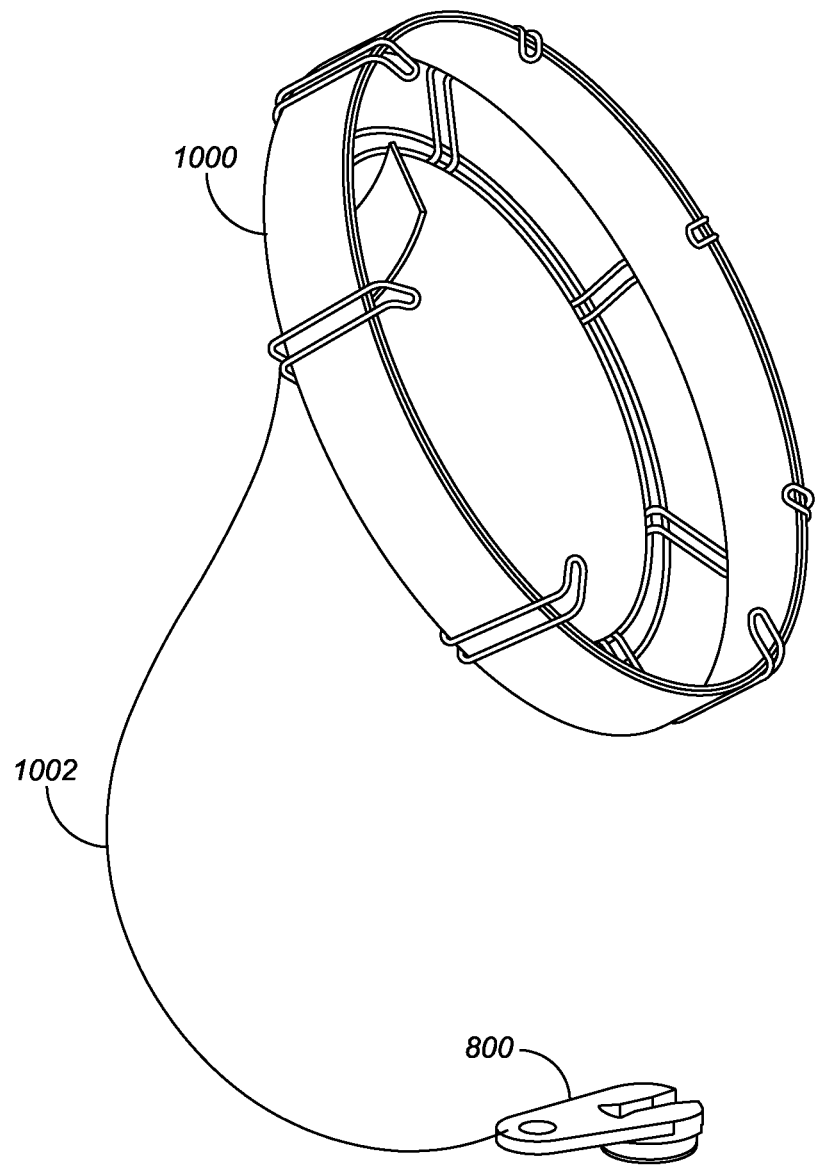
FIG. 10 illustrates an example of a column identification device tethered to its associated column.

In some cases, a sample flow component identification device may be tethered to its associated sample flow component. For example, FIG. 10 shows a column identification device (the fob 800) tethered to an associated column 1000 by means of a metallic cord or other high-temperature attachment technology 1002.

Sample flow component identification devices may include various forms of memories or indicia that are electronically, optically or magnetically readable. The memories may also be writeable. Examples of electronic memories include smart cards, flash memories, electrically erasable programmable read-only memories (EEPROMs), erasable PROMS (EPROMs), and non-volatile random access memories (NVRAMs). Examples of optical memories and indicia include optical read only or read/write memories, and one and two-dimensional bar codes. Examples of magnetic memories include magnetic discs and magnetic stripes.

In some cases, sample flow component identification devices and their corresponding identification device holders may be color-coded, or may be provided with other types of visual markers or corresponding physical features. This helps identify a correspondence between the sample flow component identification devices and their identification device holders, thereby ensuring that a user places particular types of sample flow component identification devices in particular identification device holders. Sample flow component identification devices and their corresponding identification device holders may also (or alternately) be physically shaped or sized such that particular types of sample flow component identification devices can only be inserted into particular identification device holders.

Figure 11:
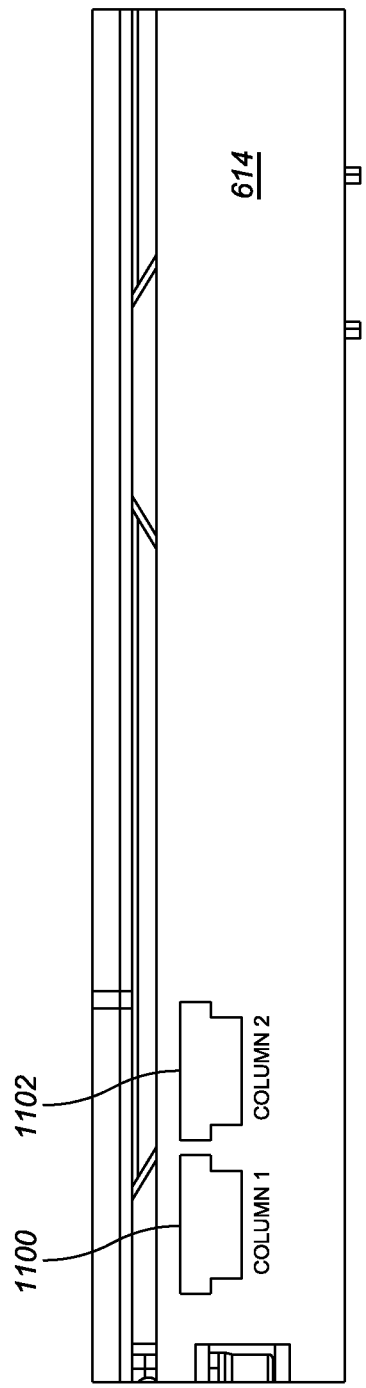
FIG. 11 illustrates a first alternate configuration of bays for the GC shown in FIG. 6.

The set of identification device holders illustrated in FIGS. 6-8 is only exemplary. Other GCs may be provided with more or fewer identification device holders (e.g., bays), and may have identification device holders corresponding to the same or different types of sample flow components. For example, FIG. 11 illustrates a first alternate configuration of bays 1100, 1102 for the GC 600. The bays 1100, 1102 are respectively labeled "Column 1" and "Column 2". Each of the bays 1100, 1102 corresponds to connection of a column in a particular sample flow path. For example, the bay labeled "Column 1"

could correspond to connection of a column in a sample flow path between the FRONT INLET and the FRONT DETECTOR of the GC 600, while the bay labeled "Column 2" could correspond to connection of a column in a sample flow path between the BACK INLET and the BACK DETECTOR of the GC 600.

In some cases, the associations between the bays 1100, 1102 and the locations of Columns 1 and 2 (within their respective sample flow paths) can be pre-configured (e.g., have default settings). For example, the GC 600 might be configured to interpret the presence of an identification device in bay 1100 as indicative that a first column is connected between the FRONT INLET and the FRONT DETECTOR. Likewise, the GC 600 might be configured to interpret the presence of an identification device in bay 1102 as indicative that a second column is connected between the BACK INLET and the BACK DETECTOR. In other cases, the associations between the bays 1100, 1102 and the locations of Columns 1 and 2 may be configurable (or programmable). For example, a user might program the GC 600 to interpret the presence of an identification device in bay 1100 as meaning a first column is connected to the FRONT INLET of the GC 600. Similarly, the user might program the GC 600 to interpret the presence of an identification device in bay 1102 as meaning a second column is connected to the BACK INLET of the GC 600. Or, for example, a user might program the GC 600 to interpret the presence of an identification device in bay 1100 as meaning a first column is connected between the FRONT INLET and a second column, and to interpret the presence of an identification device in bay 1102 as meaning a second column is connected between the first column and the FRONT DETECTOR. The bays 1100 and 1102 can also be configured in other ways.

Figure 12:
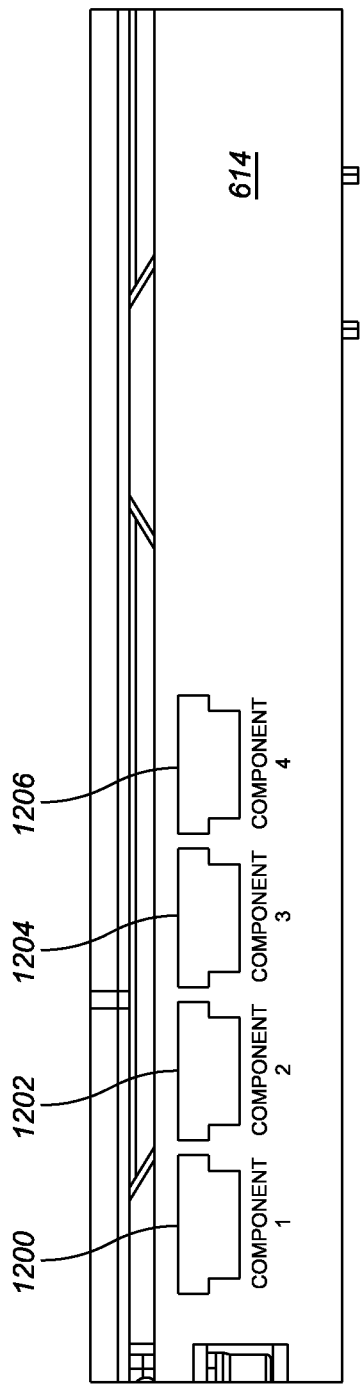
FIG. 12 illustrates a second alternate configuration of bays for the GC shown in FIG. 6.

FIG. 12 illustrates a second alternate configuration of bays 1200, 1202, 1204, 1206 for the GC 600. The bays 1200, 1202, 1204, 1206 are respectively labeled "Component 1", "Component 2", "Component 3" and "Component 4", and each bay 1200, 1202, 1204, 1206 can be associated with a particular connection of a sample flow component to the GC 600. By way of example, each bay 1200, 1202, 1204, 1206 may be configurable (or programmable) with respect to: 1) the identity of the sample flow path with which the bay is associated (e.g., FRONT INLET to FRONT DETECTOR, FRONT INLET to BACK DETECTOR, etc.); 2) the type of sample flow component with which the bay is associated (e.g., column, inlet liner, detector, etc.); and 3) the location of a sample flow component in a sample flow path (e.g., connection of a column to an inlet, connection of a column to a detector, etc.). By way of example, the labels for each of the bays 1200, 1202, 1204, 1206 may be static (e.g., printed on the panel 616) or dynamic (e.g., provided via one or more liquid crystal displays (LCDs) or color-coded light-emitting diode (LED) indicators). In addition to being user-programmable, a bay's association with a flow path, component type, or component location may be programmed by a GC method. That is, upon loading a method, a GC's control system may determine from the method that a particular sample flow component needs to be installed, and can then associate a particular bay with the particular type and location of sample flow component needed for the method.

Figure 13:
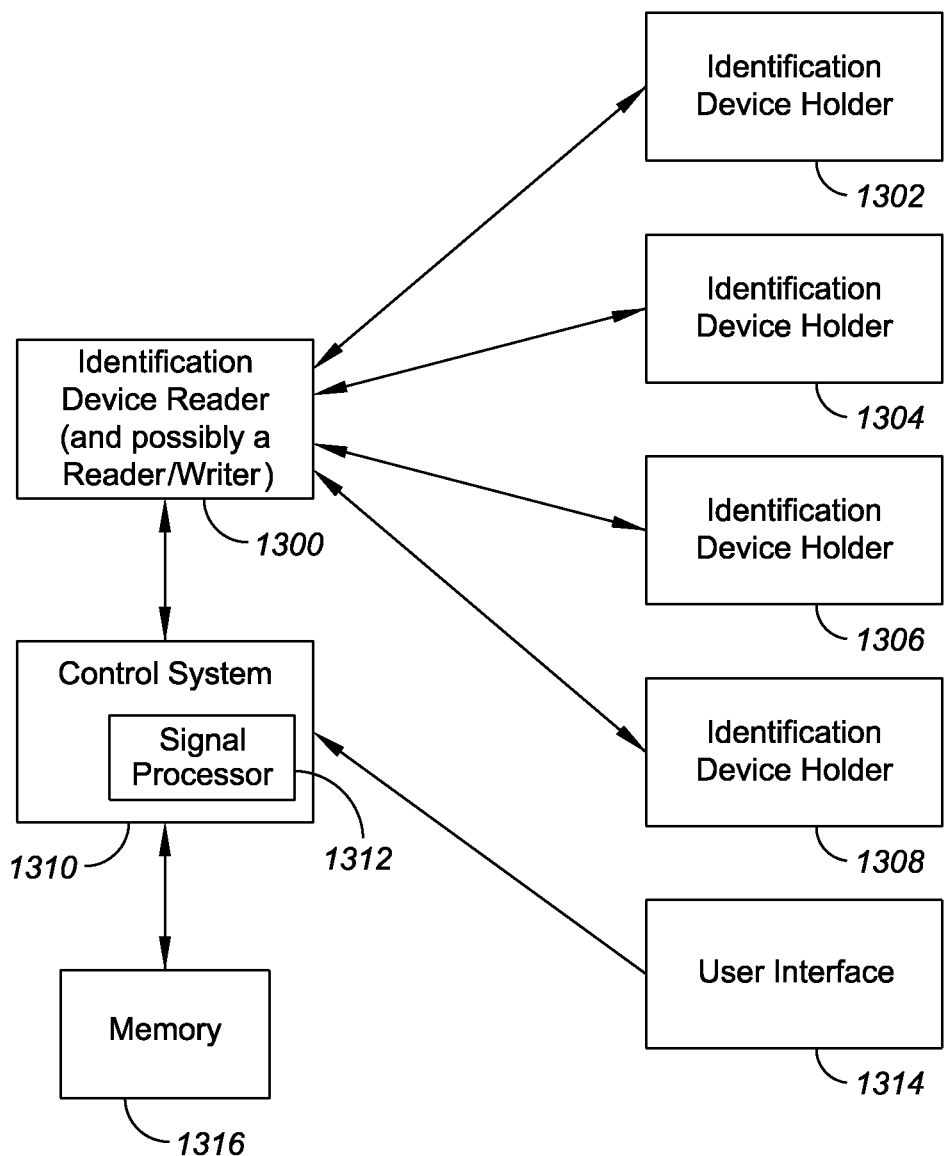
FIG. 13 provides a block diagram showing the communicative coupling of an identification device reader to each of a plurality of identification device holders.

FIG. 13 is a block diagram showing the communicative coupling of an identification device reader 1300 to each of a plurality of identification device holders 1302, 1304, 1306, 1308. Depending on the type of sample flow component identification devices being read, the identification device reader 1300 may comprise, for example, an electronic reader, an optical reader, or a magnetic reader. A wireless or radio frequency identification device (RFID) reader may also be employed, so long as it is capable of distinguishing which sample flow component identification devices are held in which identification device holders 1302, 1304, 1306, 1308.

Figure 14:
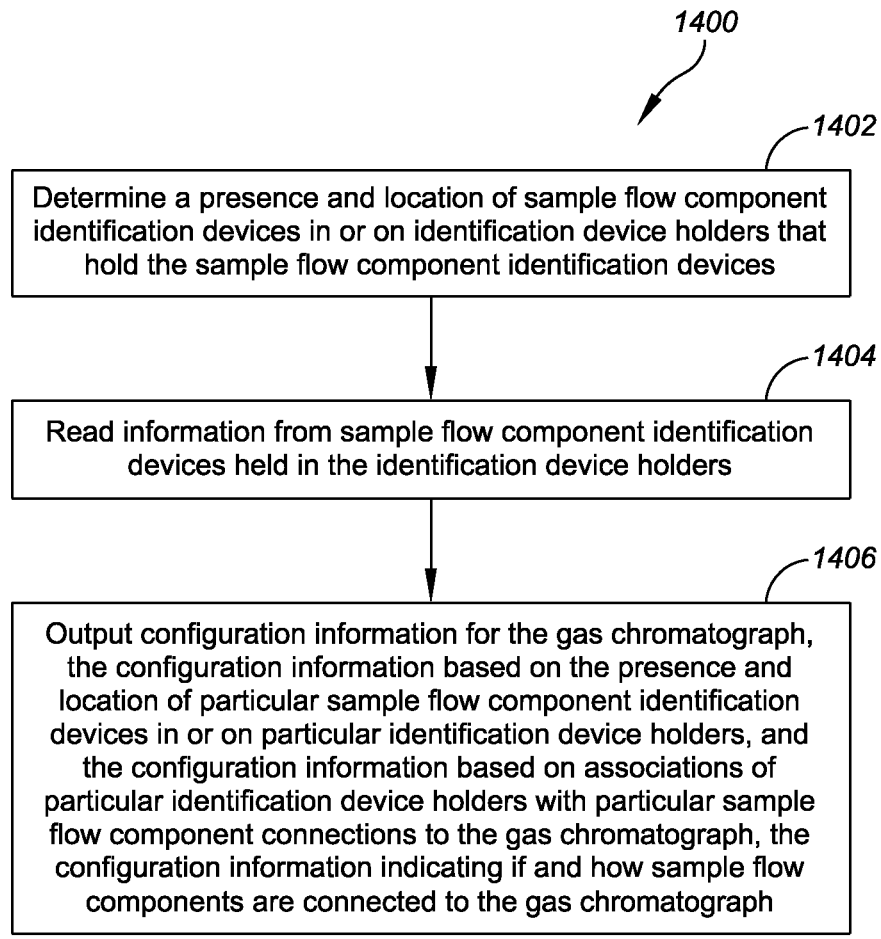
FIG. 14 illustrates an example of a method for semi-automatically configuring a GC.

The identification device reader 1300 is configured by hardware, firmware or software (e.g., a stored program of instructions) to perform the method 1400 shown in FIG. 14. The method 1400 comprises 1) determining a presence and location of sample flow component identification devices in or on the identification device holders that hold the sample flow component identification devices (at block 1402), 2) reading information from any sample flow component identification devices held in the identification device holders (at block 1404), and 3) outputting configuration information for the GC (at block 1406). As previously noted, the configuration information is based on the presence and location of particular sample flow component identification devices in or on particular identification device holders, and the associations of A) particular identification device holders with B) particular connections of sample flow components to the GC. The configuration information, in one form, may indicate if and how certain sample flow components are connected to the GC's sample flow ports. For example, the configuration information may indicate that a Column A 226 is connected between a Front Inlet 202 and a Front Detector 206, and that a Column B 228 and Column C 230 are connected between a Back Inlet 204 and a Back Detector 208 (as shown in the GC configuration of FIG. 3).

In some embodiments, the identification device reader 1300 (FIG. 13) is configured to automatically and periodically 1) determine the presence and location of sample flow component identification devices in or on the identification device holders, 2) read information from the sample flow component identification devices, and 3) output configuration information for the gas chromatograph. In other embodiments, the identification device reader 1300 is configured to perform these actions automatically upon boot: upon power up; when a user presses a button on the GC or otherwise indicates that the identification device reader 1300 should perform these actions; or at other useful times.

The information read from the sample flow component identification devices can take various forms. For example, the information can include component identification information such as a component type, component model number, component serial number, or date of component manufacture. The information can also include parametric information such as type and thickness of stationary phase, internal diameter, length, minimum and maximum operating temperatures, and absolute maximum temperature (in the case of a column), or diameter and volume (in the case of a sample injection syringe). The information may also include information pertaining to the component's use, such as the number of injections, and the time spent above the maximum operating temperature. Still further, the information may include method of use information, such as the inlet and detector types that are compatible with a particular column, or column temperature and flow information. The method of use information can include specific method parameters for a defined analytical application, or can reference a method stored by the GC (or by an external computer attached to the GC).

Some of the information that is stored in or on a sample flow component identification device may be stored on the device at the time its associated sample flow component is manufactured or tested, while other information may be stored on the sample flow component identification device (or modified) during use of its associated sample flow component. It is noted, however, that in the case of identification devices including non-writeable memories (e.g., barcodes or RFID tags), it may not be possible to save information to the device subsequent to manufacture. In these cases, the additional information can be stored elsewhere, such as on an external computer or networked database. The additional information can then be accessed using identification information stored on an identification device.

If a GC has an identification device holder with a configurable association (e.g., a configurable association with a particular flow path, component type or component location), the GC may be provided with a user interface 1314 (e.g., a knob or keypad) via which a user may program its association. Or, a GC or GC system may be provided with a software or firmware interface via which a user or GC method may program its association. The programmed association may be stored in a memory 1316 configured to receive and store programmed associations between particular identification device holders and particular installations of sample flow components in the GC. By way of example, the programmed associations stored in the memory 1316 may be read directly by the identification device reader 1300, or supplied to the identification device reader by the control system 1310.

A control system 1310 can be configured to operate the GC 600 in accord with the configuration information output by the identification device reader 1300. For example, the control system 1310 can be configured to adjust column heater control parameters (e.g., proportional, integral and derivative (PID) gains) as a function of a column's length. The control system 1310 could also adjust chromatographic parameters, such as operating temperatures and flows, based on acceptable limits that are read from (or referenced by) a column, detector or other sample flow component.

A control system may be partly or wholly housed within the GC 600 (FIG. 6), or may be partly or wholly provided by a computer that is external to the GC 600. In some embodiments, the control system 1310 shown in FIG. 13 may share some or all of its structure with the control system 122 shown in FIG. 1.

The GC 600 may further comprise a signal processor 1312 that is programmed to verify the compatibility of 1) sample flow components connected to the GC with 2) a method under which the GC 600 is to be operated. The compatibility verification can be based at least partly on the configuration information output by the identification device reader 1300. For example, the processor 1312 could verify the compatibility of a particular column or detector with a method under which the GC 600 is to be operated. The signal processor 1312 could also verify the compatibility of sample flow components with the GC 600 or with one another (e.g., the compatibility of a column with a detector). The signal processor 1312 may in some cases be a part of, or may be shared with, the control system 1310.

In some GCs, the identification device reader 1300 may be part of an identification device reader/writer. A reader/writer can be useful in that information regarding the use of a sample flow component, or information regarding changes made to a sample flow component (e.g., a change in a column's length), may be written to the sample flow component identification device that is associated with the sample flow component.

What is claimed is:

1. An apparatus, comprising:
a plurality of identification device holders for holding sample flow component identification devices associated with sample flow component, the plurality of identification device holders being connectable to a gas chromatograph, wherein particular identification device holders are associated with particular connections of sample flow components to the gas chromatograph; and
an identification device reader configured to i) determine a presence and location of sample flow component identification devices in or on the identification device holders, ii) read information from sample flow component identification devices held in the identification device holders, and iii) output configuration information for the gas chromatograph, the configuration information based on the presence and location of particular sample flow component identification devices in or on particular identification device holders, and the configuration information based on the associations of particular identification device holders with particular connections of sample flow components to the gas chromatograph, wherein the configuration information indicates if and how sample flow components are connected to the gas chromatograph.

2. The apparatus of claim 1, wherein a first of the identification device holders is associated with connection of one of the sample flow components between a first inlet and a first detector of the gas chromatograph, and wherein a second of the identification device holders is associated with connection of one of the sample flow components between a second inlet and a second detector of the gas chromatograph.

3. The apparatus of claim 2, wherein a third of the identification device holders is associated with connection of one of the sample flow components between the first inlet and the second detector of the gas chromatograph, and wherein a fourth of the identification device holders is associated with connection of one of the sample flow components between the second inlet and the first detector of the gas chromatograph.

4. The apparatus of claim 1, wherein the sample flow components include a number of inlets and a number of detectors, and two or more of the identification device holders are associated, respectively, with two or more possible sample flow paths between the number of inlets and the number of detectors.

5. The apparatus of claim 1, wherein one of the identification device holders is associated with connection of an inlet component to the gas chromatograph.

6. The apparatus of claim 1, wherein one of the identification device holders is associated with connection of a detector component to the gas chromatograph.

7. The apparatus of claim 1, wherein one of the identification device holders is associated with installation of an inlet liner in an inlet of the gas chromatograph.

8. The apparatus of claim 1, wherein one of the identification device holders is associated with connection of a sample injection syringe to an inlet of the gas chromatograph.

9. The apparatus of claim 1, wherein one of the identification device holders is associated with connection of a combined inlet, detector, and column assembly to the gas chromatograph.

10. The apparatus of claim 1, wherein:
at least three of the sample flow components are selected from a group of sample flow components consisting, of inlets and detectors, each of the at least three sample components having a respective column connection port;
one of the sample flow components is a column;
one of the sample flow component identification devices is a column identification device; and
the identification device holders include at least two identification device holders associated with respective different connections of the column to a selected inlet and a selected detector in the group of sample flow components, each of the identification device holders configured to hold the column identification device.

11. The apparatus of claim 1, wherein one of the sample flow components is a column, and wherein one of the sample flow component identification devices is a column identification device, the gas chromatograph further comprising:
the column;
the column identification device; and
a tether coupling the column identification device to the column.

12. The apparatus of claim 1, wherein one of the sample flow components is a column, and wherein one of the sample flow component identification devices is a column identification device, the gas chromatograph further comprising:
the column; and
the column identification device;
wherein the column and the column identification device have corresponding physical features identifying, a correspondence therebetween.

13. The apparatus of claim 1, wherein the plurality of identification device holders comprises a plurality of bays.

14. The apparatus of claim 1, wherein the identification device reader comprises an electronic reader.

15. The apparatus of claim 1, wherein the identification device reader comprises an optical reader.

16. The apparatus of claim 1, wherein the identification device reader is configured to automatically i) determine the presence and location of sample flow component identification devices in or on the identification device holders, ii) read information from the sample flow component identification devices, and iii) output configuration information for the gas chromatograph.

17. The apparatus of claim 1, further comprising a control system configured to operate the gas chromatograph in accord with the configuration information.

18. The apparatus of claim 1, further comprising a signal processor programmed to verify compatibility of i) sample flow components connected to the gas chromatograph with ii) a method under which the gas chromatograph is to be operated, the compatibility verification based at least in part on the configuration information.

19. The apparatus of claim 1, further comprising a housing to which the plurality of identification device holders and the identification device reader are mounted, the gas chromatograph further comprising:

a front panel, wherein at least some of the identification device holders are grouped on the front panel.

20. The apparatus of claim 1, further comprising an identification device reader/writer, of which the identification device reader is a part, the identification device reader/writer configured to write information to sample flow component identification devices held in the identification device holders.

21. The apparatus of claim 1, wherein the information that the identification device reader is configured to read includes method of use information, 22. The apparatus of claim 1, further comprising a memory, wherein:
the memory is configured to receive and store at least one programmed association between i) a particular one of the identification device holders, and ii) a particular one of the connections of sample flow components to the was chromatograph: and
the identification device reader is configured to receive the at least one programmed association from the memory.

23. A method for semi-automatically generating configuration information for a gas chromatograph, comprising:
using an identification device reader of the gas chromatograph, determining, a presence and location of sample flow component identification devices in or on identification device holders that hold the sample flow component identification devices;
reading information from sample flow component identification devices held in the identification device holders; and
outputting configuration information for the gas chromatograph, the configuration information based on the presence and location of particular sample flow component identification devices in or on particular identification device holders, and the configuration information based on associations of particular identification device holders with particular sample flow component connections to the gas chromatograph, the configuration information indicating if and how sample flow components are connected to the gas chromatograph, 24. The method of claim 23, wherein reading information from sample flow component identification devices comprises reading method of use information from at least one of the sample flow component identification devices.

* * * * *

UNITED STATES PATENT AND TRADEMARK OFFICE
CERTIFICATE OF CORRECTION

| | | |
|---|---|---|
| PATENT NO. | : 9,027,384 B2 | Page 1 of 1 |
| APPLICATION NO. | : 13/193436 | |
| DATED | : May 12, 2015 | |
| INVENTOR(S) | : Robert P. Rhodes et al. | |

It is certified that error appears in the above-identified patent and that said Letters Patent is hereby corrected as shown below:

In the Specification

In column 1, line 16, delete "use," and insert -- use. --, therefor.

In column 1, lines 52-53, delete "FIG. 10 illustrates an...... associated column;" and insert the same on Col. 1 Line 53 as a new paragraph.

In column 2, line 34, delete "net" and insert -- inlet --, therefor.

In column 7, line 19, delete "FIG, 2" and insert -- FIG. 2 --, therefor.

In column 7, line 50, delete "(Le.," and insert -- (i.e., --, therefor.

In column 11, line 38, delete "FIG, 1." and insert -- FIG. 1. --, therefor.

In the Claims

In column 11, line 65, in claim 1, delete "component," and insert -- components, --, therefor.

In column 12, line 58, in claim 10, delete "consisting," and insert -- consisting --, therefor.

In column 13, line 19, in claim 12, delete "identifying," and insert -- identifying --, therefor.

In column 14, line 11, in claim 21, delete "information," and insert -- information. --, therefor.

In column 14, lines 17-18, in claim 22, delete "was chromatograph:" and insert -- gas chromatograph; --, therefor.

In column 14, line 24, in claim 23, delete "determining," and insert -- determining --, therefor.

In column 14, line 40, in claim 23, delete "chromatograph," and insert -- chromatograph. --, therefor.

Signed and Sealed this
Twenty-ninth Day of September, 2015

Michelle K. Lee
*Director of the United States Patent and Trademark Office*